United States Patent
Bao et al.

(10) Patent No.: US 6,833,914 B1
(45) Date of Patent: Dec. 21, 2004

(54) SYSTEM AND METHOD FOR EFFICIENT SIMULATION OF REFLECTOMETRY RESPONSE FROM TWO-DIMENSIONAL GRATING STRUCTURES

(75) Inventors: Junwei Bao, Berkeley, CA (US);
Xinhui Niu, San Jose, CA (US);
Nickhil Jakatdar, Los Altos, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 443 days.

(21) Appl. No.: 10/004,495

(22) Filed: Oct. 23, 2001

(51) Int. Cl.[7] .............................................. G01N 21/88
(52) U.S. Cl. .................................................. 356/237.5
(58) Field of Search .......................... 356/237.4–237.5, 356/601; 703/6

(56) References Cited

U.S. PATENT DOCUMENTS 6,292,265 B1 * 9/2001 Finarov et al. ............. 356/630
6,614,540 B1 * 9/2003 Stirton ....................... 356/630

* cited by examiner

Primary Examiner—Richard A. Rosenberger
(74) Attorney, Agent, or Firm—Morrison & Foerster LLP

(57) ABSTRACT

The present invention relates to an efficient method for accurately simulating the integrated reflectometry response from two-dimensional grating structures using a few points. First a first and a second point are determined within an aperture located in an optical system. Next, the reflectance response of light incident at the first point and the second point are simulated. The approximated integrated reflectance response of the aperture is then determined based on the reflectance response at the first point and the second point and the weighted average of the reflectance response at the first point and the second point.

51 Claims, 13 Drawing Sheets

SYSTEM AND METHOD FOR EFFICIENT SIMULATION OF REFLECTOMETRY RESPONSE FROM TWO-DIMENSIONAL GRATING STRUCTURES

TECHNICAL FIELD

The present invention relates to the simulation of the reflectometry response from grating profiles and more particularly to an efficient method for accurately simulating the integrated reflectometry response from two-dimensional grating structures using a few points.

BACKGROUND ART

Spectroscopic reflectometry and ellipsometry have been a mainstay for thin film metrology for many years. Recently, spectroscopic reflectometry and ellipsometry have been applied to characterizing patterned structures in integrated circuit (IC) processing by directing a beam of light on the patterned structures at a certain angle of incidence and measuring the spectra of the reflected light. However, due to the difficulty of rigorous simulation responses from patterned structures, empirical methods, such as neural networks (NN) or principle component analysis (PCA), are used to build up the relation between the patterned structure parameters (e.g., width of a structure (CD), grating height, sidewall angle, and other profile parameters) and reflected spectra.

FIG. 1 illustrates a typical reflectometry configuration for characterizing patterned structures located on a wafer. A broadband light beam 105 travels through an optical system 110 characterized by a numerical aperture. A lens 115 focuses the broadband light beam 105 into a spot characterized by a spot size onto a patterned structure located on wafer 120 (note that throughout this specification a lens is referred to more generically as an aperture). The light reflected off of the patterned structure located on wafer 120 is then collected by lens 115 and transmitted to a spectrometer 125 through optical system 110. Using other metrology tools, such as a scanning electron microscope (SEM), an atomic force microscope (AFM), etc., the parameters of the patterned structure can be measured off-line. Next, neural networks or principal component analysis can be used to build up (train) a non-linear relation between the reflected spectra and the parameters of the patterned structure. However, the relation between the reflected spectra and the parameters of the patterned structure is only valid when the values of the parameters are within the range of parameters used for training. Furthermore, long turnaround times imposed by off-line metrology also result in lower yields, slower learning curves, and higher costs for new processes and products.

A multi-point rigorous simulation method can be used to avoid doing experiments to build up empirical relations between the reflected spectra and the parameters of patterned structures. Ideally, the numerical aperture should be very small (e.g. less than 0.01) so that the reflectometry response can be simulated using normal incidence. However, if the lens 115 is too small, then the light throughput is low, thus weakening the intensity of the light beam 105 incident on a two-dimensional grating structure. The weaker the intensity of the light beam 105, the longer it takes to collect enough simulation data to achieve stability.

Starting from Maxwell's equations, the response of light reflected from patterned structures can be simulated rigorously using numerical methods. However, in an actual reflectometry system, to have an acceptable spot size (less than 100 $\mu m$) and throughput (less than 1 second), the numerical aperture (NA) is fairly large (about 0.05 or larger). Thus, the reflectance is actually the integrated response from multiple beams of light reflected off the patterned structures, where the incidence angle of each light beam is close to zero degrees. FIGS. 2a and 2b show an example of the multi-point rigorous simulation method. FIG. 2a shows light passing through numerous (e.g., 20 to 30) points 205 across an aperture 210 creating numerous light beams 215. The aperture 210 focuses each light beam 215 onto the two-dimensional grating structure 220 at an angle close to zero degrees. Simulating the numerous light beams 215 focused onto the two-dimensional grating structure 220 yields the response distribution 225 for light beams 215 as shown in FIG. 2b. The integrated response for this wavelength very closely approximates the actual reflectance and can be obtained by adding up each of the responses shown in FIG. 2b. However, the simulation takes a long time.

A single point rigorous simulation method can also be used to avoid doing experiments to build up empirical relations between the reflected spectra and the parameters of the patterned structures. FIGS. 3a and 3b show an example of the single point rigorous simulation method. FIG. 3a shows a simulation of light passing through a single point O 305 located at the center of an aperture 310 creating a single light beam 315. The light beam 315 is incident on the two-dimensional grating structure 320 at an angle of zero degrees. FIG. 3b shows the simulated reflectance response 325 of the light passing through the single point O 305. Although, the reflectance response 325 can be obtained very quickly, it is not very accurate since it only represents the reflectance response 325 from light passing through the single point O 305. The reflectance response 325 does not take into account the reflectance response from light passing through other points across the aperture 310, and thus cannot represent the overall reflectance response of the aperture 310.

FIG. 4 is a simulation which compares the accuracy of the response from light reflected off of a two-dimensional grating structure using the multi-point rigorous simulation method and the single point simulation method. As shown in FIG. 4, the simulated response 410 obtained using the single point rigorous simulation method differs greatly from the response 405 obtained using the multi-point rigorous simulation method. The multi-point rigorous simulation method closely approximates the actual reflectance response. Thus, there is a desire for a method of simulating the reflectance response of two-dimensional grating structures that is both accurate and not time consuming.

SUMMARY OF INVENTION

The method in accordance with embodiments of the present invention relates to a method for efficient simulation of reflectometry response from two-dimensional grating structures.

In one embodiment, the light intensity distribution across the aperture is uniform. A first and a second point are determined within an aperture located in an optical system. Next, the reflectance response of light incident at the first point and the second point are simulated. The approximated integrated reflectance response of the aperture is then determined based on the reflectance response at the first point and the second point and determined characteristics of the optical system.

In another embodiment, the light intensity distribution across the aperture is not uniform. A first and a second point are determined within an aperture located in an optical system. Next, the reflectance response of light incident at the first point and the second point are simulated. The approximated integrated reflectance response of the aperture is then determined based on the reflectance response at the first point and the second point and determined characteristics of the optical system.

BRIEF DESCRIPTION OF DRAWINGS

FIG. 2b shows a plot of the reflectance response obtained using the multi-point rigorous simulation method illustrated in FIG. 2a.

FIG. 3a illustrates the prior art single point rigorous simulation method for simulating the response from a single light beam reflected off of a two-dimensional grating structure. FIG. 3b shows a plot of the reflectance response obtained using the single point rigorous simulation method illustrated in FIG. 3a.

DETAILED DESCRIPTION

The present invention provides a method for efficient simulation of reflectometry response from two-dimensional grating structures. In the following description, numerous details are set forth in order to enable a thorough understanding of the present invention. However, it will be understood by those of ordinary skill in the art that these specific details are not required in order to practice the invention. Further, well-known elements, devices, process steps and the like are not set forth in detail in order to avoid obscuring the present invention.

Although the invention has been described in conjunction with particular embodiments, it will be appreciated that various modifications and alterations may be made by those skilled in the art without departing from the spirit and scope of the invention. The invention is not to be limited by the foregoing illustrative details, but rather is to be defined by the appended claims.

As stated above, there are a number of ways to simulate the reflectometry response of the two dimensional grating structure. However, each of the prior art methods for simulating the reflectometry response of the two dimensional grating structure are either too costly, too time consuming, not accurate enough, or a combination, thereof Thus, there is a desire for an efficient method for simulating the reflectometry response of two-dimensional grating structures that overcomes the problems associated with the prior art. The present invention discloses a method for deriving the k-angle quadrature for numerical aperture integration for a two-dimensional grating structure, where k is the number of simulation angles used to approximate the reflectometry response of the two-dimensional grating structure.

Figure 1:
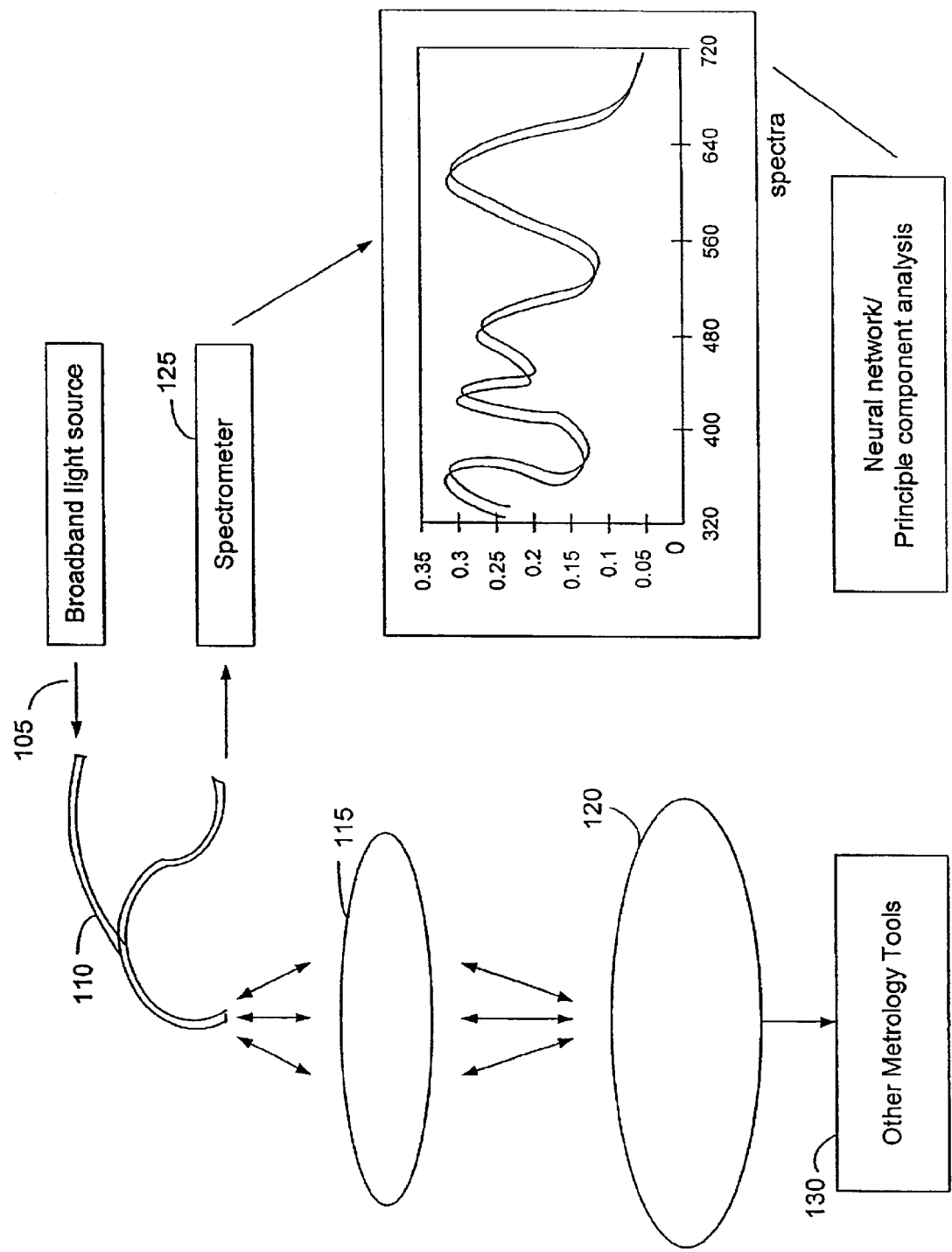
FIG. 1 shows a typical reflectometry configuration for characterizing patterned structures located on a wafer.
Figure 2A:
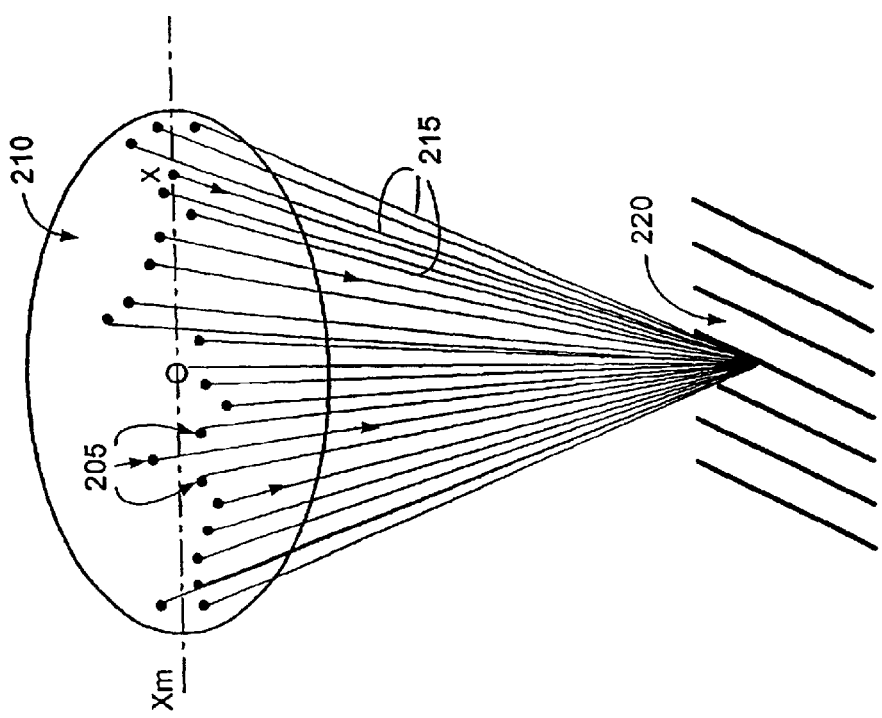
FIG. 2a illustrates the prior art multi-point rigorous simulation method for simulating the response from light reflected off of a two-dimensional grating structure.
Figure 2B:
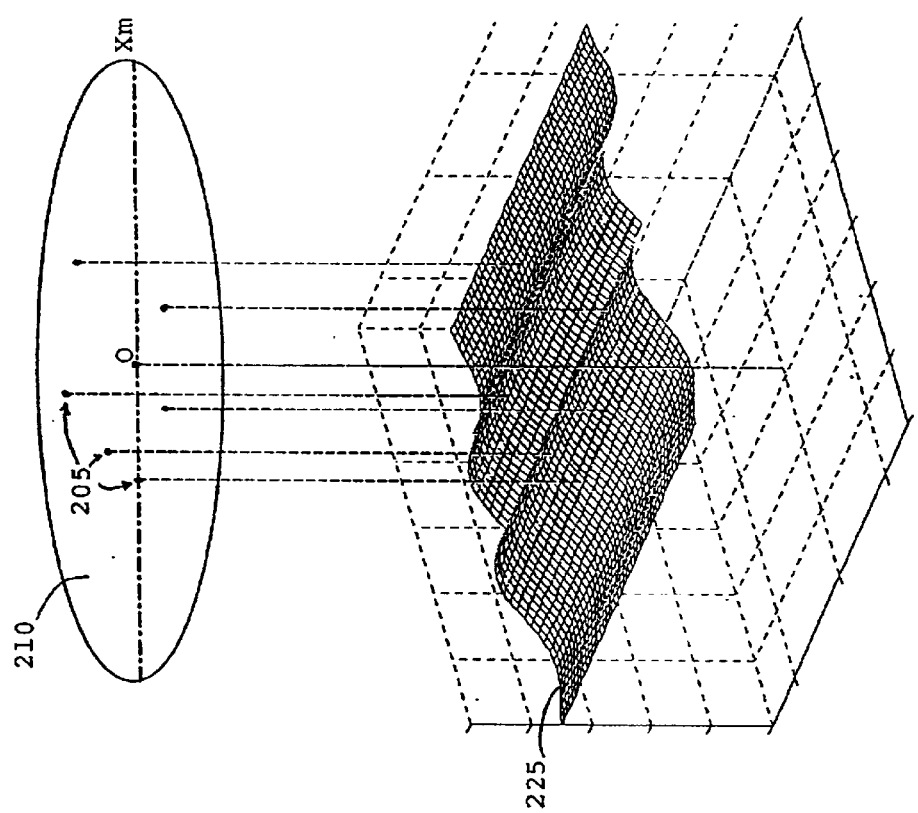
Figures 3A, 3B:
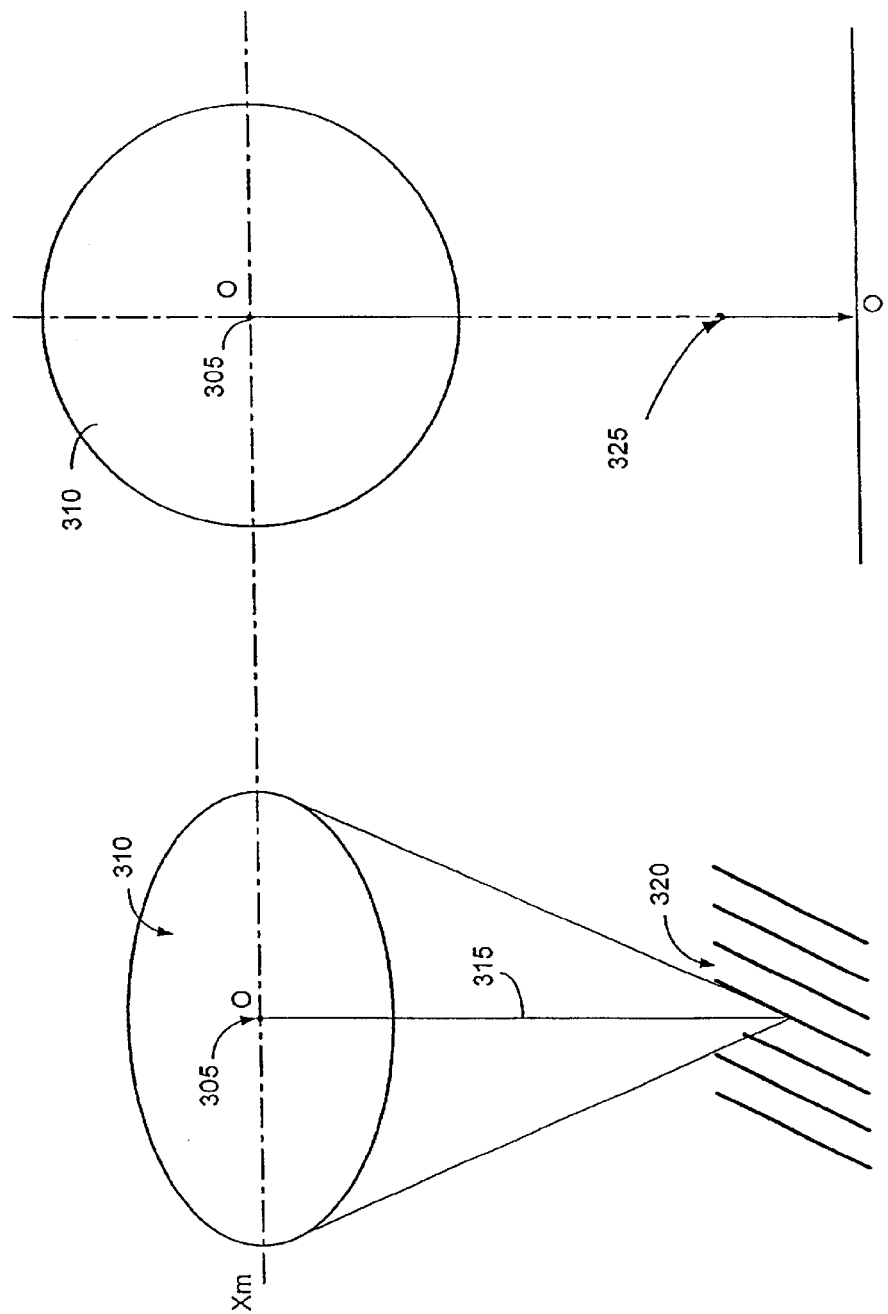
Figure 4:
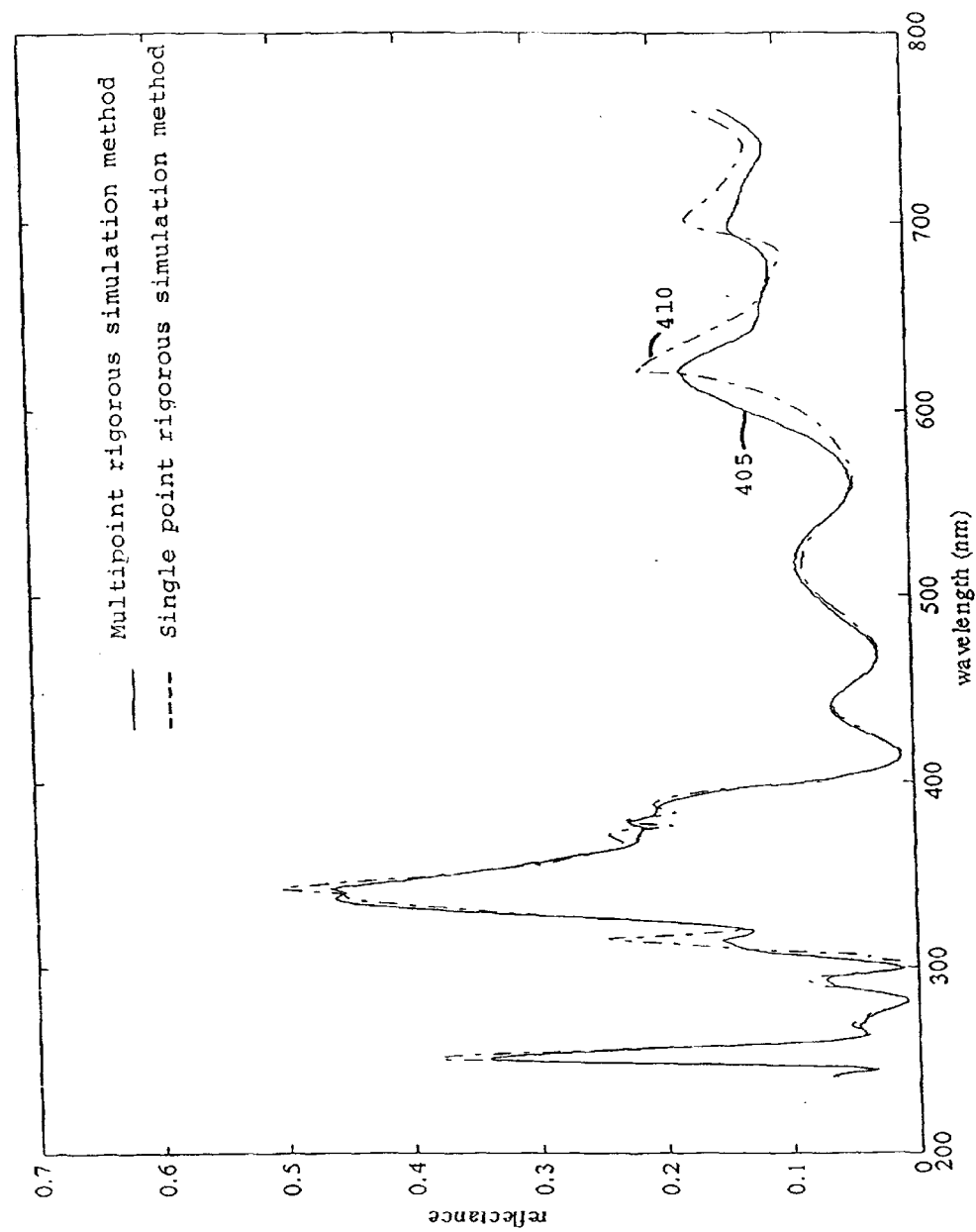
FIG. 4 shows a simulation comparing the accuracy of the simulated response from light reflected off of a two-dimensional grating structure using the multi-point rigorous simulation method and the single point rigorous method.
Figures 5A, 5B:
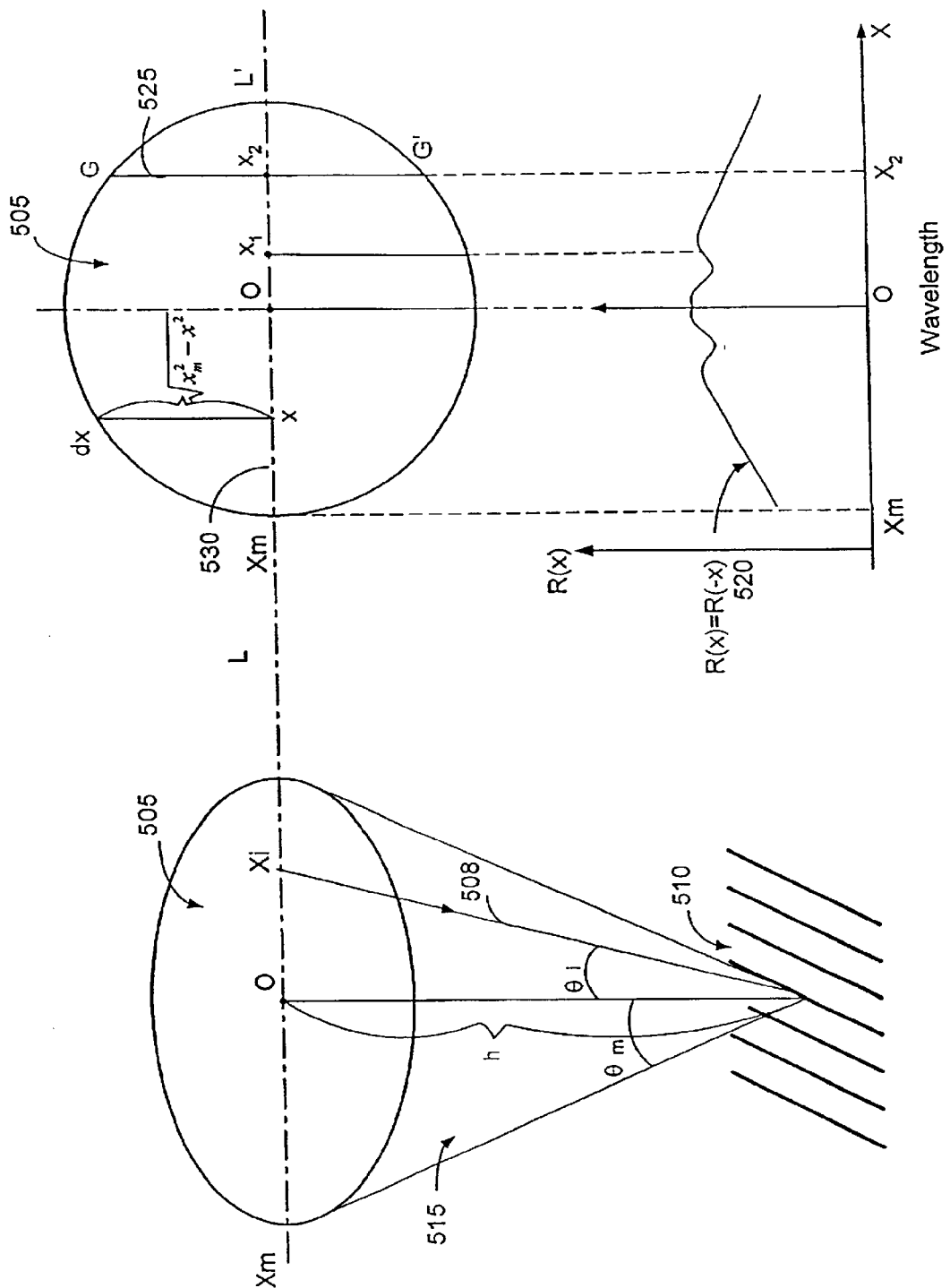
FIG. 5a shows a lens focusing a light beam passing through point $x_i$ onto a two-dimensional grating structure, where the angle of the light beam incident on the two-dimensional grating structure is $\theta_i$.
FIG. 5b shows an example of a 2-angle quadrature method for simulating the integrated response from light reflected off of a two-dimensional grating structure.

FIG. 5a shows an aperture 505 focusing a light beam 508 passing through point $x_i$ onto a two-dimensional grating structure 510. The angle of the light beam 508 incident on the two-dimensional grating structure 510 is $\theta_i$. The numerical aperture of the optical system is defined as $n(\sin \theta_m)$, where n is the refractive index of the medium and $\theta_m$ is the half-angle of the cone 515 formed as light is focused through the aperture 505 onto the two-dimensional grating structure 510. The test grating area for many integrated circuits is generally only 100 $\mu$m or less in size. Therefore, the spot size of the light beam 508 incident on the two-dimensional grating structure 510 located within the test grating area must also be very small. If the spot size of the light beam 508 is larger than the test grating area, light may reflect off other features located on the integrated circuit, thus distorting the desired reflectance response of the two-dimensional grating structure 510. Generally, the value of the half-angle $\theta_m$ is determined by the measurement tools used to measure the two-dimensional grating structures 510 and can be obtained from the measurement tool manufacturer.

To simplify the math used to derive the k-angle quadrature for numerical aperture integration for a two-dimensional grating structure 510 in a first embodiment of the present invention, some assumptions and premises are made. First, an assumption is made that the intensity of the light incident on the aperture 505 is uniformly distributed The information as to whether or not the light distribution is actually uniformly distributed across the aperture 505 can be obtained from the manufacturer of the metrology tool. Note, however, that in a second embodiment of the present invention, if the actual light intensity distribution across the aperture 505 is not uniform, but can be measured, the measured light intensity distribution can be used as weight in determining the k-angle quadrature for numerical aperture integration for a two-dimensional grating structure. The second embodiment of the present invention is explained further below.

To further simplify the math used to derive the k-angle quadrature, a first premise is made that if the two-dimensional grating structure 510 is substantially parallel (which includes parallel) to the line GG' 525 located on the aperture 505 as shown in FIG. 5b, then the reflectance response of each light beam 508 passing through any point along the line GG' 525 and onto the two-dimensional grating structure 510 is approximately the same. This premise can be verified using rigorous simulation on a computer (see discussion of FIGS. 6-7 below).

Figure 6:
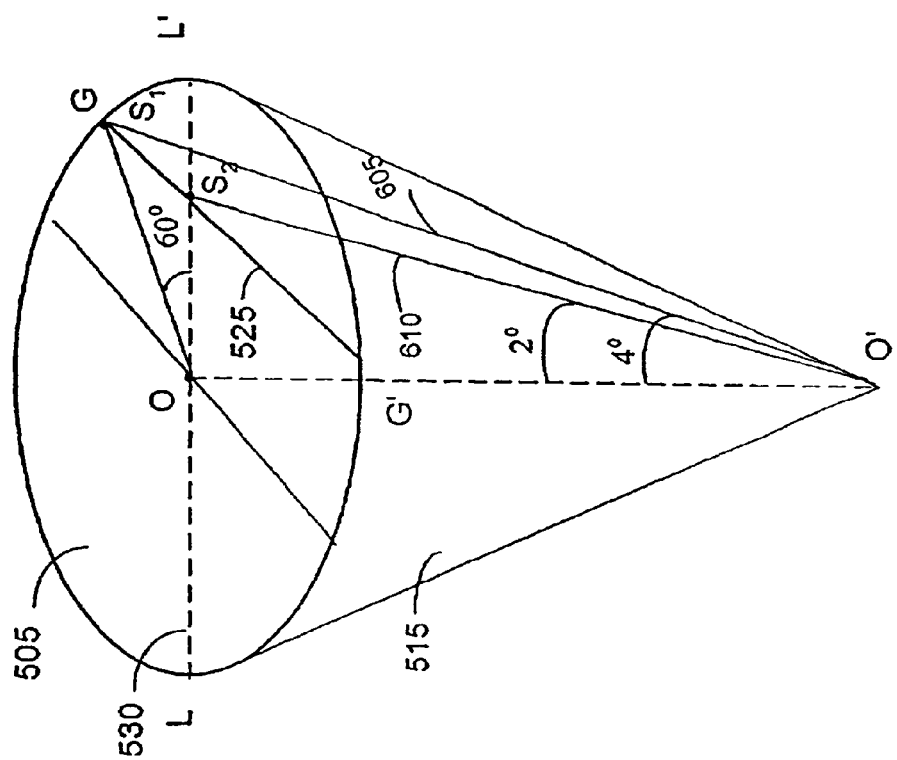
FIG. 6 shows a three dimensional view, of an aperture having two incidence angles along the line GG' which is parallel to a two-dimensional grating structure.

FIG. 6 shows a three-dimensional view of the aperture 505 having a line GG' 525 parallel to the two-dimensional grating structure 510 (shown in FIG. 5a) and a horizontal line LL' 530 across the center of the aperture 505 and perpendicular to the line GG' 525. Two points $s_1$ and $s_2$ are also shown along the line GG' 525, where $s_2$ is located at the intersection of the lines LL' 530 and GG' 525. The incident angle of the unpolarized light beam 605 passing through the point $s_1$ is four degrees and the incident angle of the unpolarized light beam 610 passing through the point $s_2$ is two degrees. To verify the first premise, the reflectance response of the light beam 605 passing through the point $s_1$ and the light beam 610 passing through the point $s_2$ are simulated using the multi-point rigorous simulation method and shown in FIG. 7.

Figure 7:
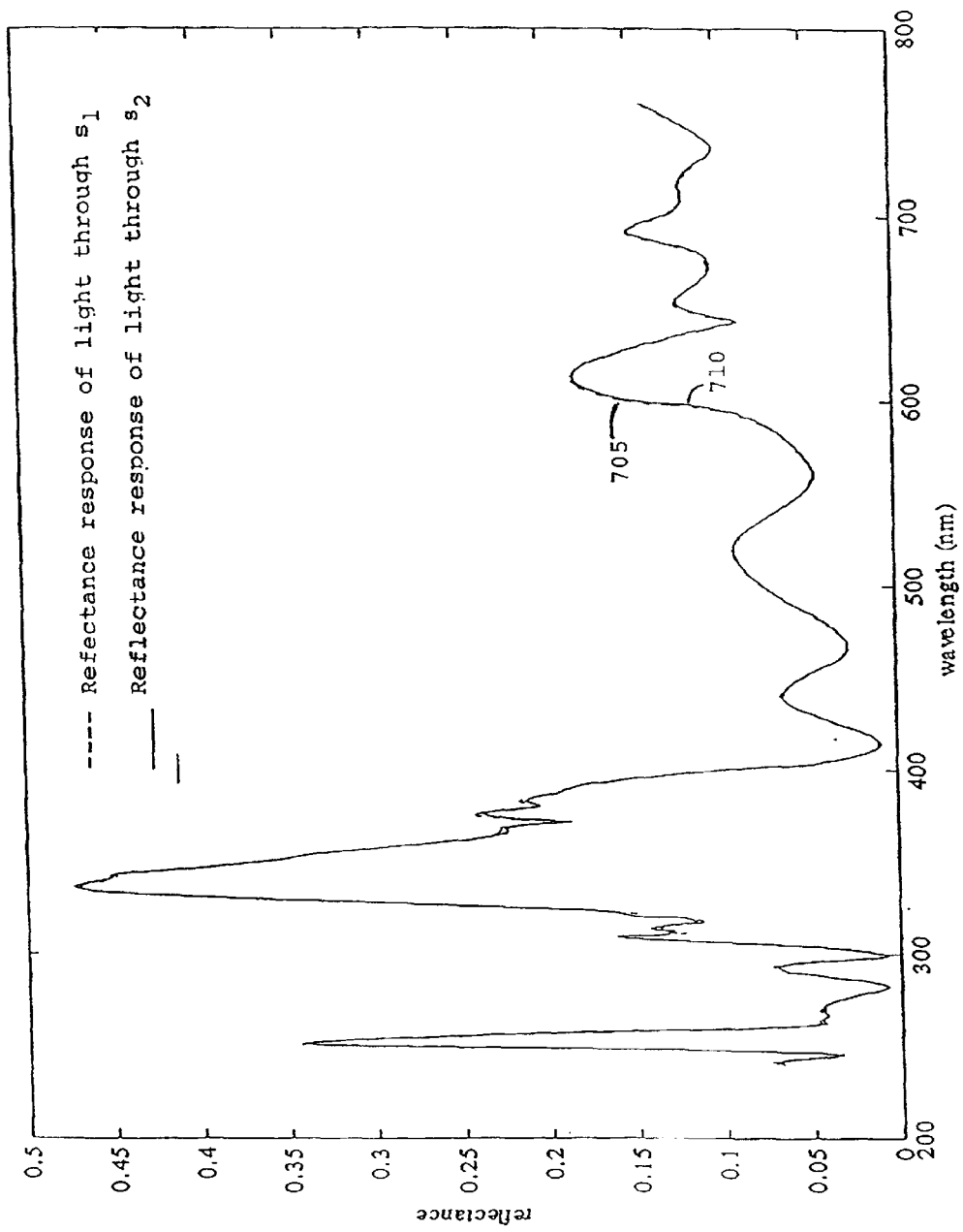
FIG. 7 shows a simulation comparing the reflectance response of light passing through two points, $s_1$ and $s_2$, along a line parallel to a two-dimensional grating structure.

FIG. 7 shows that the reflectance response 705 of the light passing through point $s_1$ and the reflectance response 710 of light passing through point $s_2$ located on along the line GG' 525 are almost the same, thus validating the first premise stated above. The reflectance responses for light beams passing through other points along the line GG' 525 can also be simulated and compared to further validate this premise. Therefore, the reflectance response of light passing through only one point on the line GG' 525 approximates the reflectance response for the entire line GG' 525 if the line GG' 525 is parallel to the two-dimensional grating structure 510. This is true for any line within the aperture 505 that is parallel to the two-dimensional grating structure 510 and if needed, can be verified using rigorous simulation.

In one embodiment, the point chosen to simulate the reflectance response for each line within the aperture 505 parallel to the two-dimensional grating structure 510 is located at the center of each respective line. For example, the preferred point for approximating the reflectance response for the line GG' 525 is the point $s_2$. Note, however, that each point located at the center of each line within the aperture 505 parallel to the two-dimensional grating structure 510 will have a different reflectance measurement. Thus, all that is required to approximate the reflectance of the entire aperture 505 is to simulate the reflectance response of light passing through every point along the line LL' 530.

To even further simplify the math used to derive the k-angle quadrature, a second premise is made that the reflectance response R(x) for any wavelength from the two-dimensional grating structure 510 along the direction of the line, LL' 530 can be approximated by using a set of orthonormal functions, such as polynomials, Fourier series, or any other orthogonal and normal function sets. For example, since the reflectance response 525 is continuous and symmetrical about the point O 503, a $(4k-2)^{th}$ order even polynomial function can be used. If k=2, then R(x) is a $6^{th}$ order polynomial even function as shown in equation (1) below:

$$R(x) = a_0 + a_2\left(\frac{x}{x_m}\right)^2 + a_4\left(\frac{x}{x_m}\right)^4 + a_6\left(\frac{x}{x_m}\right)^6 \quad (1)$$

Where $a_i$ (i=0,1,2 . . . ) depends on wavelength and the two-dimensional grating structure 510. The number of orders needed depends on how fast the reflectance R(x) changes along the line LL' 530. For a numerical aperture of a typical reflectometer (e.g., approximately 0.1 or less) and most two-dimensional grating structures, this condition is satisfied for k=2 or 3.

Figure 8:
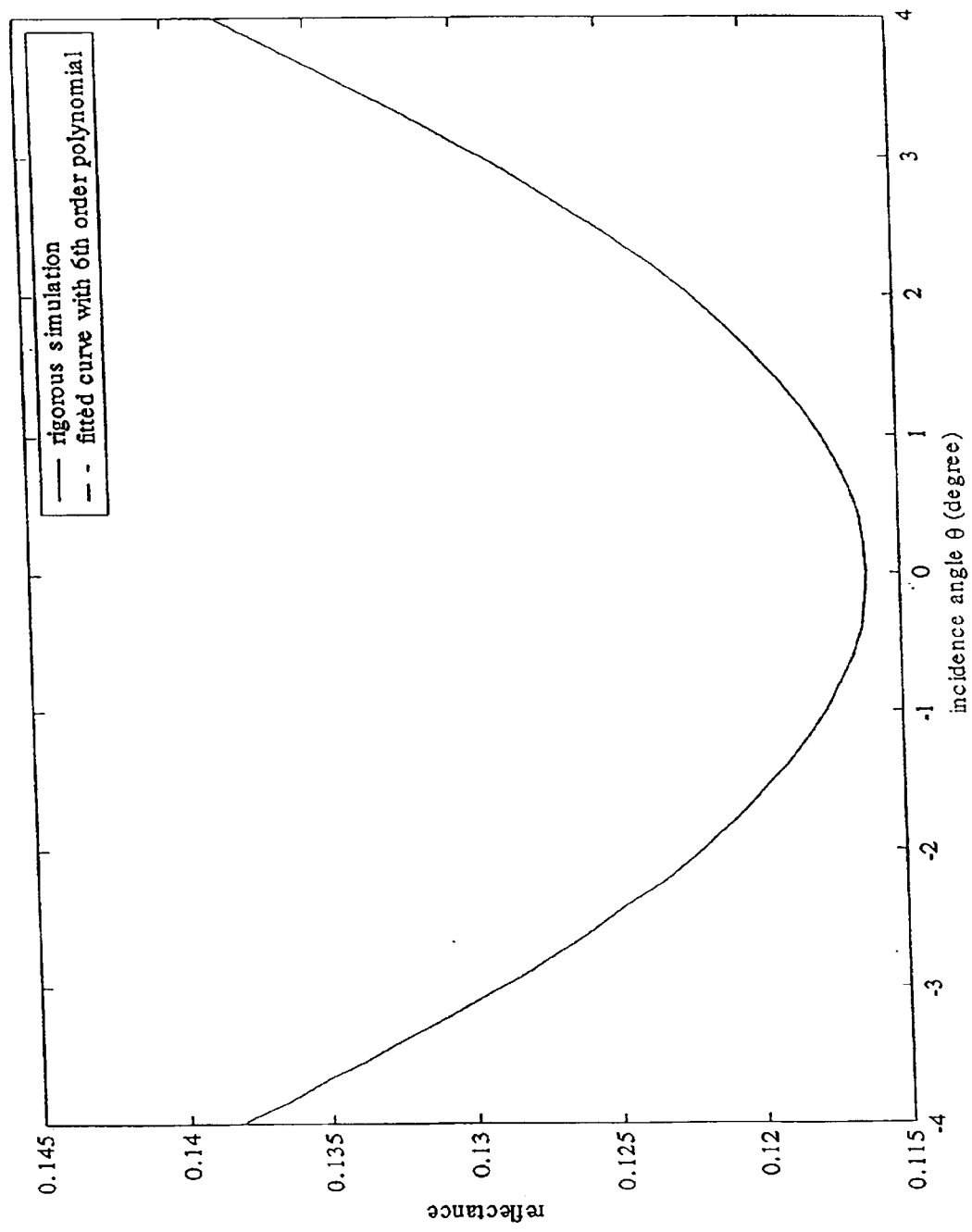
FIG. 8 shows a simulation comparing the simulated response from light reflected off of a two-dimensional grating structure using the multi-point rigorous simulation method and an approximation of the simulated response curve using a 6th order even polynomial function.

This second premise can be verified by simulating the response from multiple light beams (e.g., 10) reflected off of the two-dimensional grating structure 510 using the prior art multi-point rigorous simulation method on a computer, where the light beams focused onto the two-dimensional grating structure 510 pass through multiple points (e.g., 10) located along the line LL' 530. Once the reflectance response from the multiple points are simulated, the next step is to approximate the resulting curve of the reflectance response with a $(4k-2)^{th}$ order even polynomial function as illustrated in FIG. 8 for k=2. As stated above, for a numerical aperture of a typical reflectometer (approximately 0.1 or less) and most two-dimensional grating structures, this second premise is satisfied for k=2 or 3. However, it should be noted that k is preferably equal to a value sufficient to approximate the polynomial for the resulting wavelength. Thus, if the second premise is not satisfied for k=2 or 3, higher values of k can be used.

Figure 9:
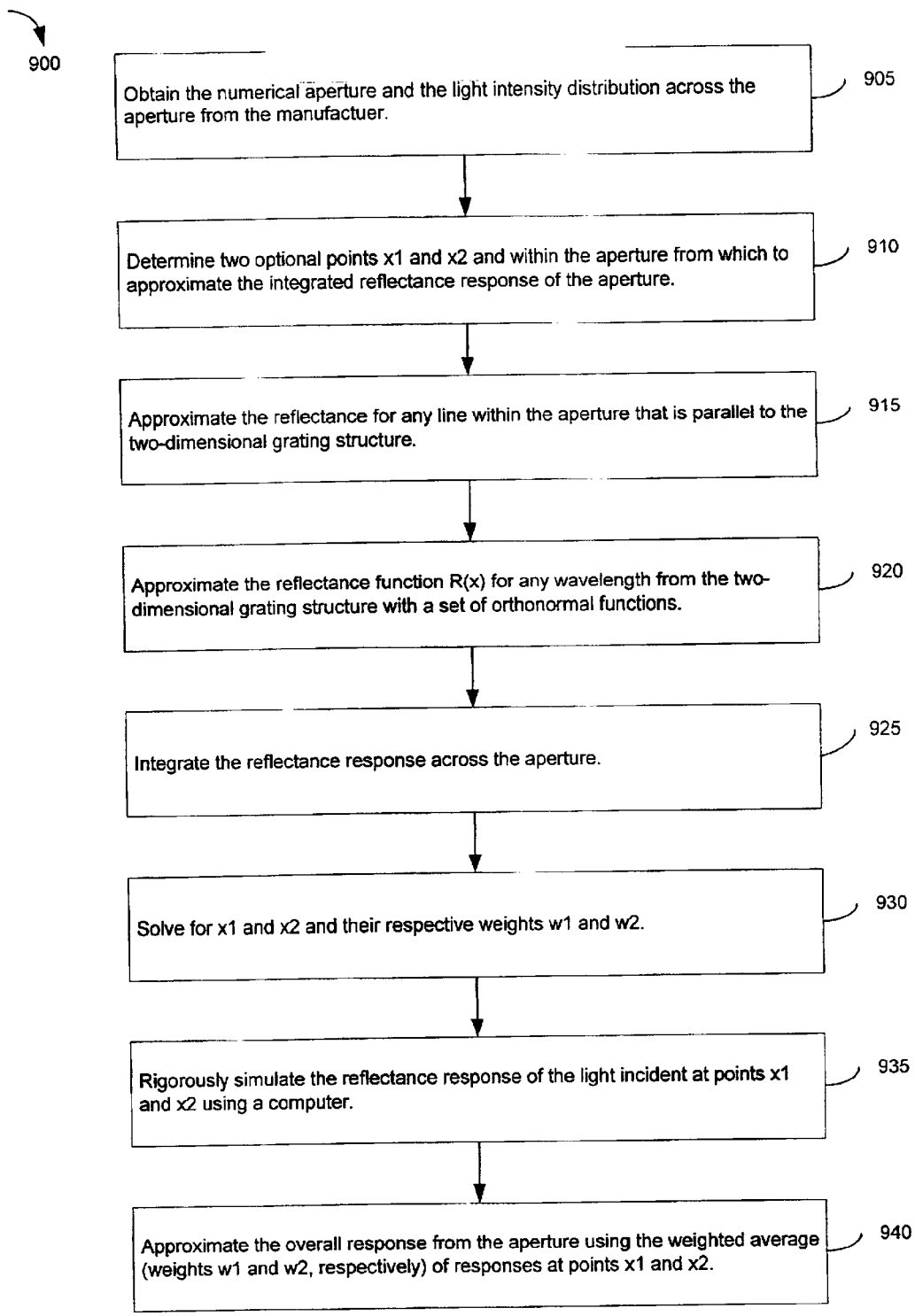
FIG. 9 shows a flow chart overview of a process to derive the k-angle quadrature for numerical aperture integration for a two-dimensional grating structure where the light intensity distribution across the aperture is uniform.

FIG. 9 shows a flow chart overview 900 of a process to derive the k-angle quadrature for numerical aperture integration for a two-dimensional grating structure. The first step 905 in deriving of the k-angle quadrature for numerical aperture integration for a two-dimensional grating structure is to obtain the numerical aperture of the optical system and the light intensity distribution across the aperture 505 from the manufacturer of the metrology tool. Note that the numerical aperture and the light intensity distribution across the aperture 505 can also be measured. For purposes of this embodiment, it is assumed that the light distribution within the aperture 505 is uniform, the numerical aperture of the optical system is approximately 0.1 or less, and k=2, i.e., the 2-angle quadrature is used to approximate the integrated reflectance response. However, in other embodiments, the numerical aperture can be greater than 0.1 and for other values of k, the derivation can be generalized accordingly.

The next step 910 is to determine two optimal points, $x_1$ and $x_2$, along the line LL' 530 from which to approximate the integrated reflectance response of the aperture 505. The weight of the reflectance response from the two light beams passing through optimal points $x_1$ and $x_2$ is determined to approximate the reflectance response of the entire aperture 505. The weights for the light intensity distribution at optimal points $x_1$ and $x_2$ are $w_1$ and $w_2$, respectively. An equation using the weighted average of reflectance responses from points $x_1$ and $x_2$ to approximate the integrated reflectance across the aperture 505 is shown in equation (2) below.

$$\int_0^{x_m} R(x) \cdot \sqrt{x_m^2 - x^2} \cdot 4 \cdot dx = [w_1 R(x_1) + w_2 R(x_2)] \cdot \pi x_m^2, \quad (2)$$

where R(x) is the reflectance at any incidence angle along the line LL' 530, $\sqrt{x_m^2-x^2}dx$ is the weight of the area at position x along the line LL' 530, and $x_m$ is the length of the line OL'. The value of $x_m$ can be calculated from the value of numerical aperture.

Note that making the assumption that the intensity of the light is uniformly distributed across the aperture 505 simplifies equation (2) by eliminating an additional term specifying the weight due to any non-uniform distribution of light across the aperture 505. Eliminating the additional term specifying the weight due to any non-uniform distribution of light across the aperture 505 ensures a closed-form analytical solution of the integral on the left hand side of equation (2). However, it should be noted that there can also be a closed-form analytical solution of the integral on the left hand side of equation (2) in some cases where the light distribution is not uniform.

In step 915, the first premise is made that response of light passing through only one point on any line within the aperture 505 that is parallel to the two-dimensional grating structure 510 is sufficient to approximate the reflectance response for that line within the aperture 505 if that line is parallel to the two-dimensional grating structure 510. Again, this first premise can be verified using rigorous simulation on a computer as described above. In step 920, the second premise is made that that the reflectance response R(x) for any wavelength from the two-dimensional grating structure 510 along the direction of the line LL' 530 can be approximated by a set of orthonormal functions, such as polynomials, Fourier series, or any other orthogonal and normal function sets. For example, since the reflectance response 525 is continuous and symmetrical about the point O 503, a $(4k-2)^{th}$ order even polynomial function can be used. If k=2, then R(x) is a $6^{th}$ order polynomial even function as shown in equation (1) above. Again, the second premise can be verified by simulating the response from multiple light beams (e.g., 10) reflected off of the two-dimensional grating structure 510 using the prior art multi-point rigorous simulation method on a computer as described above.

In step 925, substitute R(x) from equation (1) into R(x) of equation (2) and then perform the integration which yields equation (3) below:

$$(w_1 + w_2 - 1)a_0 + \left(w_1 t_1^2 + w_2 t_2^2 - \frac{1}{4}\right)a_2 + \left(w_1 t_1^4 + w_2 t_2^4 - \frac{1}{8}\right)a_4 + \left(w_1 t_1^6 + w_2 t_2^6 - \frac{5}{64}\right)a_6 = 0 \quad (3)$$

where $$t_i = \frac{x_i}{x_m}, (i = 1, 2).$$

Since equation (3) should be valid for any value of $a_i$ (i=0,1,2, . . . ), their coefficients should be equal to 0 as shown below.

$$w_1 + w_2 - 1 = 0 \quad (4)$$

$$w_1 t_1^2 + w_2 t_2^2 - 1/4 = 0 \quad (5)$$

$$w_1 t_1^4 + w_2 t_2^4 - 1/8 = 0 \quad (6)$$

$$w_1 t_1^6 + w_2 t_2^6 - \frac{5}{64} = 0 \quad (7)$$

In step 930, solving equations (4) through (7) yields one solution set for $w_1$, $w_2$, and $t_1$ and $t_2$ having real physical meaning:

$$\begin{cases} w_1 = 0.723607 \\ w_2 = 0.276393 \\ t_1 = 0.309017 \\ t_2 = 0.809017 \end{cases}$$

However, note that solving equations (4) through (7) may yield multiple solution sets for $w_1$, $w_2$, and $t_1$ and $t_2$ having real physical meaning. Considering the relation between $t_i$ and incidence angle $\theta_i$ yields:

$$t_i = \frac{\tan\theta_i}{\tan\theta_m}, \quad (8)$$

therefore, $$\theta_i = \arctan\{t_i \cdot \tan[\arcsin(NA)]\} \quad (9).$$

For example, if NA=0.07, then $\theta_1$=1.2422, $\theta_2$=3.2492. However, NA could be any value sufficient to make the previously stated assumptions and premises valid.

Once the values of $\theta_1$, $\theta_2$, $w_1$ and $w_2$ are calculated for a particular numerical aperture, the values $w_1$, $w_2$, $\theta_1$, and $\theta_2$ can then be used to rigorously simulate the reflectance response of the light incident at points $x_1$, and $x_2$ using a computer in Step 935. The reflectance response values $R(x_1)$ and $R(x_2)$ are then obtained from the resulting rigorous simulation. Finally the values for $R(x_1)$, $R(x_2)$, $w_1$ and $w_2$ are used to calculate the weighted average to represent the integrated response from the aperture 505 in step 940.

$$w_1 R(x_1) + w_2 R(x_2) \quad (10)$$

Figure 10:
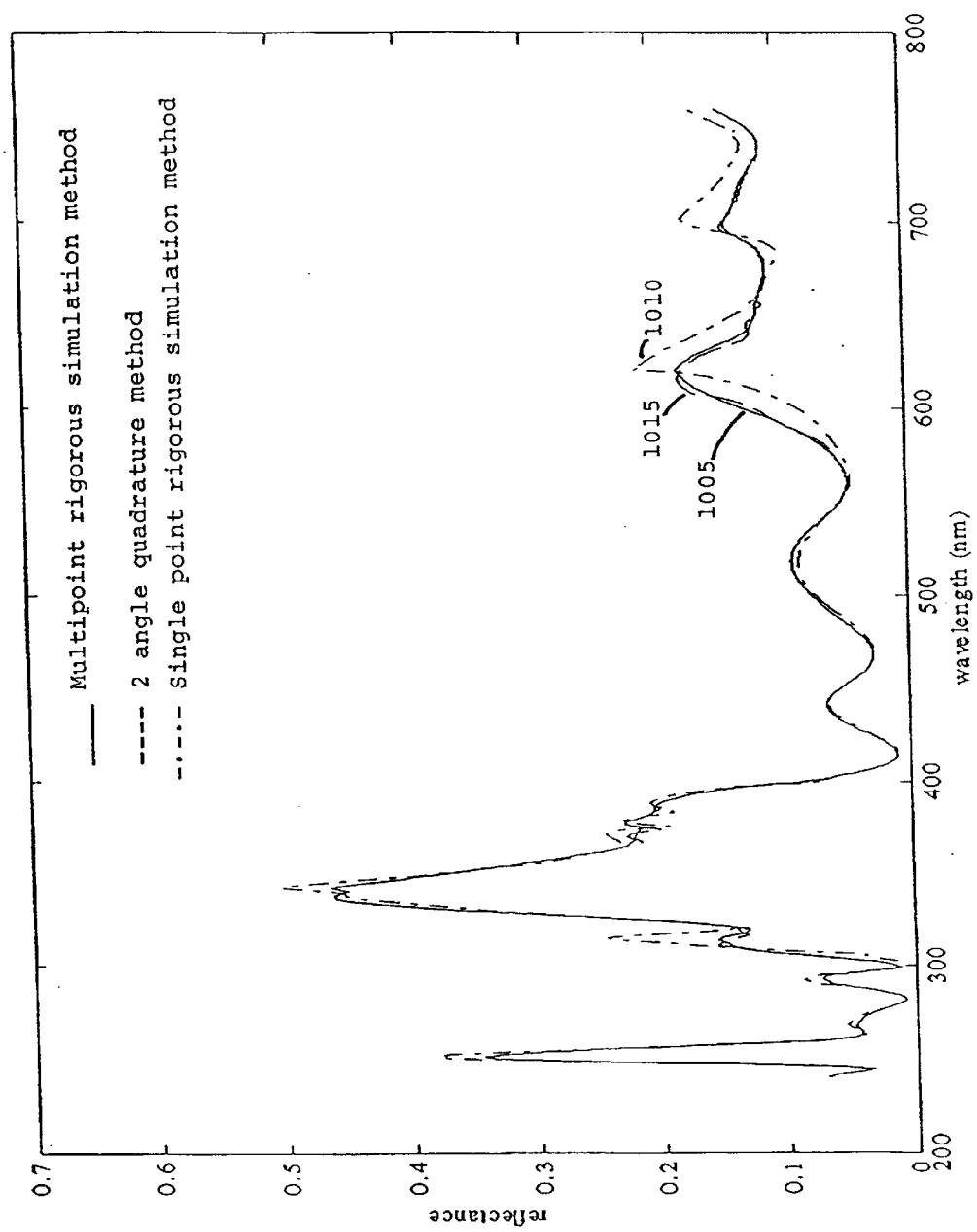
FIG. 10 shows a simulation comparing the accuracy of the simulated response from light reflected off of a two-dimensional grating structure using the multi-point rigorous simulation method, the single point rigorous method, and the 2-angle quadrature method.

FIG. 10 shows a simulation comparing the results of the simulated reflectance response across the aperture 505 from a two-dimensional grating structure using the prior art multi-point rigorous method (accurate simulation) 1005, the prior art single-point rigorous method (0 degree incidence) 1010, and the k-angle quadrature method 1015 in accordance with an embodiment of the present invention where k=2. The plot shown in FIG. 10 shows that the simulated reflectance response of the aperture 505 using the 2-angle quadrature method very closely approximates the simulated reflectance response of the aperture 505 using the prior art multi-point rigorous simulation method. The simulation shown in FIG. 10 also shows that the simulated reflectance response of the aperture 505 using the 2-angle quadrature method is significantly more accurate than simulated reflectance response of the aperture 505 using the prior art single point rigorous simulation method. Thus, the k-angle quadrature method of the present invention provides a significant advantage over the prior art multi-point rigorous simulation method by very closely approximating the simulated reflectance response of the aperture 505 twenty to thirty times more quickly. Similarly, the k-angle quadrature method of the present invention provides a significant advantage over the prior art single point rigorous simulation method by quickly and accurately approximating the reflectance response of the aperture 505. Furthermore, the k-angle quadrature method provides a significant advantage over the prior art in that once the values of $x_1$, $x_2$, $\theta_1$, $\theta_2$, $w_1$ and $w_2$ are calculated for a particular numerical aperture, the overall integrated reflectance response across the aperture 505 can be determined for any two-dimensional grating structure using only k-angles.

Figure 11:
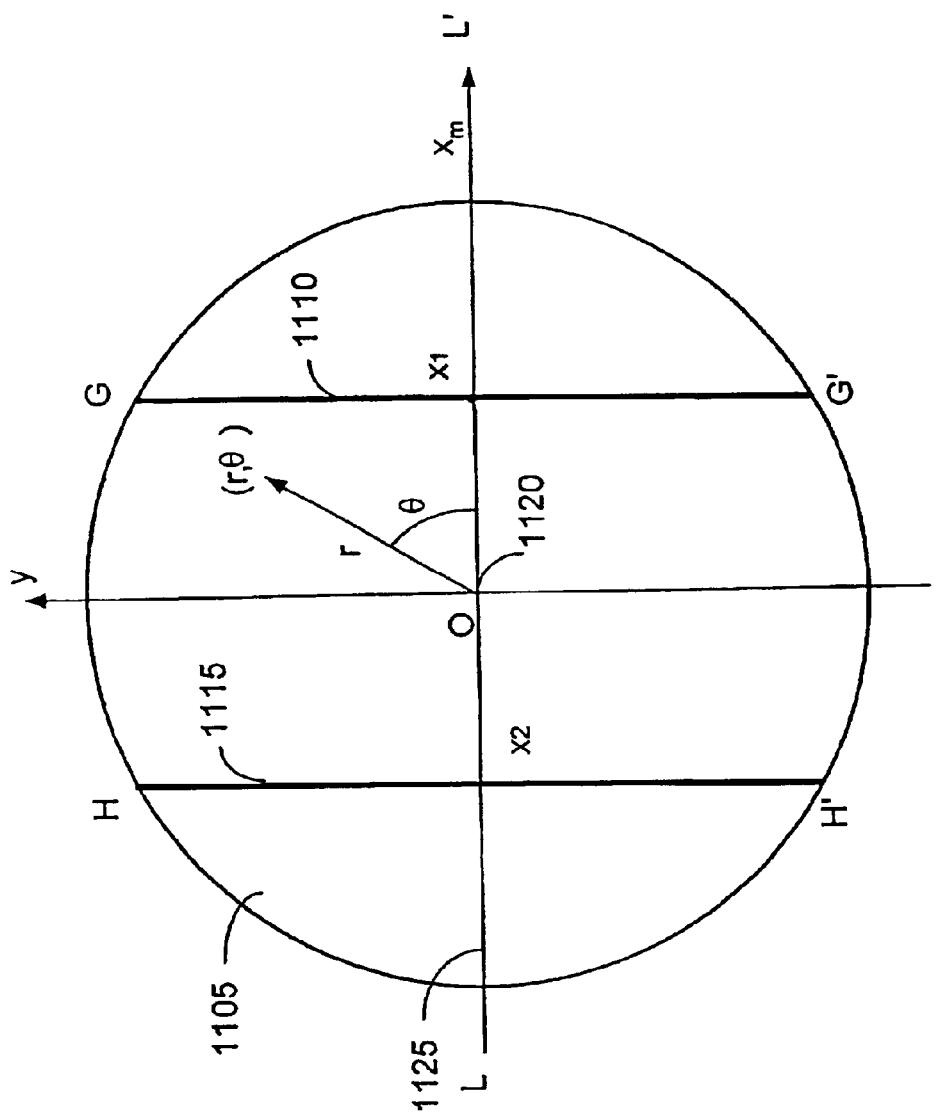
FIG. 11 shows an example of the 2-angle quadrature method for simulating the integrated response from light reflected off of a two-dimensional grating structure, where the light intensity distribution across the aperture is not uniform.

FIG. 11 illustrates a second embodiment of the present invention where the light distribution within the aperture 1105 is not uniform. Although the light distribution within the aperture 1105 is not uniform, the same method for deriving the k-angle quadrature for numerical aperture integration for a two-dimensional grating structure disclosed in the first embodiment can be used if the actual light intensity distribution across the aperture 1105 can be measured. The measured intensity distribution of the light incident on the aperture 1105 is used as weight in equation (2) in place of the weight term $\sqrt{x_m^2-x^2}dx$. In addition, numerical integration may be needed.

Figure 12:
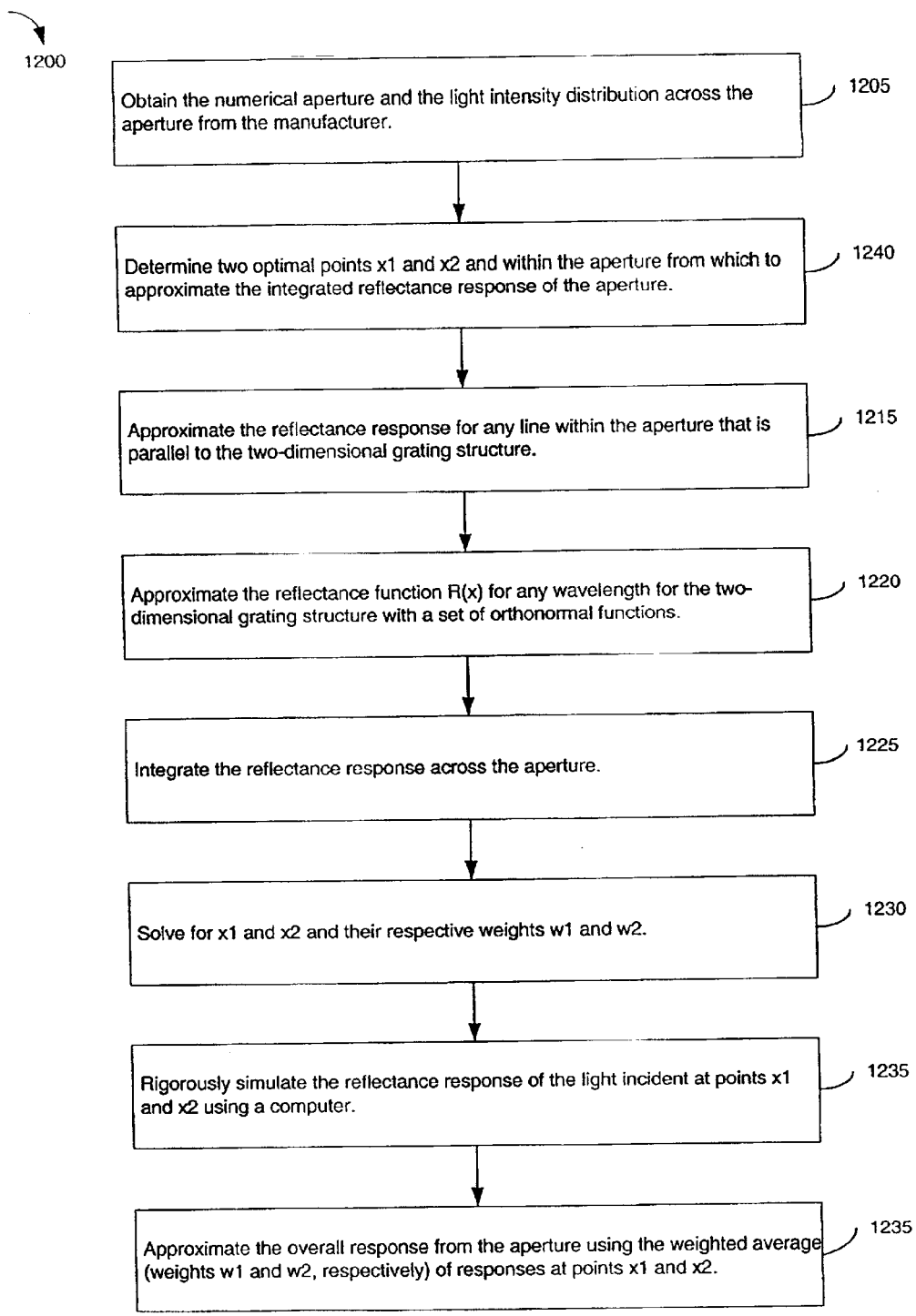
FIG. 12 shows a flow chart overview of a process to derive the k-angle quadrature for numerical aperture integration for a two-dimensional grating structure where the light intensity distribution across the aperture is not uniform.

FIG. 12 illustrates a flow chart overview 1200 of a process to derive the k-angle quadrature for numerical aperture integration for a two-dimensional grating structure. The first Step 1205 is to obtain the numerical aperture of the optical system and the light intensity distribution across the aperture 1105 from the manufacturer of the metrology tool. Note that the numerical aperture and the light intensity distribution can also be measured. For purposes of this example, it is assumed that the light distribution within the aperture 1105 is not uniform, the numerical aperture of the optical system is approximately 0.1 or less, and k=2, i.e., the 2-angle quadrature is used to approximate the integrated reflectance response. However, in other embodiments, the numerical aperture can be greater than 0.1 and for other values of k, the derivation can be generalized accordingly.

In Step 1210, the first premise, as stated above, is used to simplify the math. If a two-dimensional grating structure is parallel to the line GG' 1110, then the reflectance response of each light beam passing through any point along the line GG' 1110 and onto the two-dimensional grating structure is almost the same. Likewise, if the two-dimensional grating structure is parallel to the line HH' 1115, then the reflectance response of each light beam passing through any point along the line HH' 1115 and onto the two-dimensional grating structure is almost the same. This first premise can be verified using rigorous simulation on a computer as discussed in FIGS. 6-7 above. Therefore, the reflectance response of light passing through only one point is sufficient to approximate the reflectance response for the entire line GG' 1110 or line HH' 1115. This first premise is true for any line within the aperture 1105 that is parallel to a two-dimensional grating structure. In a preferred second embodiment, the point chosen to simulate the reflectance response for each line within the aperture 1105 parallel to the two-dimensional grating structure is located at the center of each respective line. For example, the preferred point for approximating the reflective response for the line GG' 1110 is the point $x_1$ and the preferred point for approximating the reflective response of the line HH' 1115 is the point $x_2$. Note, however, that each point located at the center of each line within the aperture 1105 parallel to the two-dimensional grating structure will have a different reflectance measurement.

In Step 1215, the second premise, as stated above, is used again to even further simplify the math used to derive the k-angle quadrature. The reflectance response R(x) for any wavelength from the two-dimensional grating structure along the direction of the line LL' 1125 can be approximated by a set of orthonormal functions, such as polynomials, Fourier series, or any other orthogonal and normal function sets. In this particular embodiment, a $(4k-2)^{th}$ order even polynomial function can be used since the reflectance response is continuous and symmetrical about the point O 503. For example, if k=2, then R(x) is a $6^{th}$ order polynomial even function as shown in equation (11) below:

$$R(x) = a_0 + a_2\left(\frac{x}{x_m}\right)^2 + a_4\left(\frac{x}{x_m}\right)^4 + a_6\left(\frac{x}{x_m}\right)^6 \quad (11)$$

Where $a_i$ (i=0,1,2 . . . ) depends on wavelength and the two-dimensional grating structure. The number of orders needed depends on how fast the reflectance R(x) changes along the line LL' 1125. For a numerical aperture of a typical reflectometer (e.g., approximately 0.1 or less) and most two-dimensional grating structures, this condition is satisfied for k=2 or 3. This second premise can be verified as discussed above and shown in FIG. 8.

The next Step 1220 is to determine two optimal points, $x_1$ and $x_2$, along the line LL' 1125 from which to approximate the integrated reflectance response of the aperture 1105. The weight of the reflectance from the two light beams passing through the optimal incidence angles $x_1$ and $x_2$ is also be determined to approximate the reflectance response of the entire aperture 1105.

As stated above, the light distribution incident on the aperture 1105, is not uniform, but can be measured. The non-uniform distribution of light on aperture 1105 can be specified with a function I(x, y) or I(r,θ), where r and θ are the radial and the angular coordinates, respectively. Thus, the weight term $\sqrt{x_m^2-x^2}dx$ on the left hand side of the integral in equation (2) can be replaced with a new weight term w(x)dx representing the measured intensity distribution of the light incident on the aperture 1105.

The weight term w(x)dx representing the measured intensity distribution of the light incident on the aperture 1105 is equal to the amount of the light passing through line GG' 1110 having a width dx plus the amount of light passing through the line HH' 1115 having a width dx. Note that line GG' 1110 located at position $x_1$ and line HH' 1115 located at position $x_2$ are both symmetric about the center 1120 of the aperture 1105. Therefore, weight term w(x)dx can be written as $$w(x)dx = \pi x_m^2 dx \int_{-\sqrt{x_m^2-x^2}}^{\sqrt{x_m^2-x^2}} I(x,y)dy, \quad (12)$$

where the light distribution function I(x,y) satisfies the normalization condition $$\iint_{aperture} I(x,y)dxdy = 1. \quad (13)$$

For example, if the light distribution function is a circularly symmetric function:

$$I(x,y) = I(r,\theta) = \frac{1}{K}\left[1 - \frac{1}{2}\frac{r^2}{x_m^2}\right], \quad (14)$$

where the normalization factor k is $K=3/4\pi x_m^2$, then due to the circular symmetry of the light distribution function, the weight term is:

$$w(x)dx = 4\pi x_m^2 dx \int_0^{\sqrt{x_m^2-x^2}} I(x,y)dy \quad (15)$$

-continued $$= \frac{4}{K} dx \sqrt{x_m^2 - x^2} \left( \frac{5}{6} - \frac{1}{3} \frac{x^2}{x_m^2} \right).$$

Replacing the weight term $\sqrt{x_m^2-x^2}dx$ on the left hand side of equation (2) with the weight term in equation (15) above yields:

$$\int_0^{x_m} R(x)w(x)\,dx = \frac{4}{K} \pi x_m^2 \int_0^{x_m} R(x) \sqrt{x_m^2 - x^2} \left( \frac{5}{6} - \frac{1}{3} \frac{x^2}{x_m^2} \right) dx. \quad (16)$$

where $R(x)$ is the reflectance for the light beam passing through point x along the line LL' 1125, $$w(x)dx = \frac{4}{K} dx \sqrt{x_m^2 - x^2} \left( \frac{5}{6} - \frac{1}{3} \frac{x^2}{x_m^2} \right) \quad (17)$$

is the weight of the area at position x along the line LL' 1125, and $x_m$ is the length of the line OL' 1125.

In Step 1225, substitute $R(x)$ from equation (11) into $R(x)$ of equation (16) and then performing the integration yields equation (18) below:

$$(w_1 + w_2 - 1)a_0 + \left(w_1 t_1^2 + w_2 t_2^2 - \frac{2}{9}\right)a_2 + \\ \left(w_1 t_1^4 + w_2 t_2^4 - \frac{5}{48}\right)a_4 + \left(w_1 t_1^6 + w_2 t_2^6 - \frac{1}{16}\right)a_6 = 0 \quad (18)$$

where $t_i = \frac{x_i}{x_m}, (i = 1, 2).$

Since the above equation should be valid for any value of $a_i$ (i=0,1,2, ... ), their coefficients should be equal to 0 as shown below.

$$w_1+w_2-1=0 \quad (19)$$

$$w_1 t_1^2+w_2 t_2^2-2/9=0 \quad (20)$$

$$w_1 t_1^4+w_2 t_2^4-5/48=0 \quad (21)$$

$$w_1 t_1^6+w_2 t_2^6-1/16=0. \quad (22)$$

In Step 1230, solving equations (19) through (22) yields one solution set for $w_1$, $w_2$, and $t_1$ and $t_2$ having real physical meaning:

$$\begin{cases} w_1 = 0.247517 \\ w_2 = 0.752483 \\ t_1 = 0.296618 \\ t_2 = 0.793932 \end{cases}$$

However, note that solving equations (19) through (22) may yield multiple solution sets for $w_1$, $w_2$, and $t_1$ and $t_2$ having real physical meaning. Considering the relation between $t_i$ and incidence angle $\theta_i$ yields:

$$t_i = \frac{\tan\theta_i}{\tan\theta_m}, \quad (23)$$

therefore, $$\theta_i = \arctan\{t_i \cdot \tan[\arcsin(NA)]\}. \quad (24)$$

For example, if NA=0.07, then $\theta_1$=1.1924, $\theta_2$=3.1888. However, NA could be any value sufficient to make the previously stated assumptions and premises valid.

Once the values of $\theta_1$, $\theta_2$, $w_1$ and $w_2$ are calculated for a particular numerical aperture, the values $w_1$, $w_2$, $\theta_1$, and $\theta_2$ can then be used rigorously simulate the reflectance responses of light beams passing through points $x_1$, and $x_2$ using a computer in Step 1235. The reflectance response values $R(x_1)$ and $R(x_2)$ are then obtained from the resulting simulation. Finally the values for $R(x_1)$, $R(x_2)$, $w_1$ and $w_2$ are used to calculate the weighted average to represent the integrated response from the aperture 505 in step 1240.

$$w_1 R(x_1)+w_2 R(x_2) \quad (25)$$

Thus, the k-angle quadrature method of the present invention provides a significant advantage over the prior art multi-point rigorous simulation method by very closely approximating the simulated reflectance response of the aperture 1105 twenty to thirty times more quickly. Similarly, the k-angle quadrature method of the present invention provides a significant advantage over the prior art single point rigorous simulation method by quickly and accurately approximating the reflectance response of the aperture 1105. Furthermore, the k-angle quadrature method provides a significant advantage the over the prior art in that once the values of $x_1$, $x_2$, $\theta_1$, $\theta_2$, $w_1$ and $w_2$ are calculated for a particular numerical aperture, the overall integrated reflectance response across the aperture 1105 can be determined for any two-dimensional grating structure using only k-angles.

What is claimed is:

1. A method of determining an approximated integrated response across an aperture within an optical system from light reflected off of a two-dimensional grating structure, comprising the steps of:
   determining a first and second point within said aperture;
   simulating a reflectance response of said light incident only at said first point and said second point; and
   determining an approximated integrated reflectance response of said aperture based on said reflectance response only at said first point and said second point and determined characteristics of said optical system.

2. The method of claim 1, further comprising the steps of:
   obtaining the numerical aperture of said optical system;
   obtaining the light intensity distribution across said aperture; and
   using a set of orthonormal functions to approximate a reflectance response for any wavelength from said two-dimensional grating structure.

3. The method of claim 2, when said orthonormal function is one of a polynomial or a Fourier series.

4. The method of claim 3, wherein said orthonormal function is one of a $(4k-2)^{th}$ even polynomial function.

5. The method of claim 4, wherein k is a value sufficient such that when used, said $(4k-2)^{th}$ even polynomial function approximates said reflectance response for said resulting wavelength.

6. The method of claim 1, wherein the step of determining said first point and said second point includes determining said first point along a first line substantially parallel to said two-dimensional grating structure and determining said second point along a second line substantially parallel to said two-dimensional grating structure.

7. The method of claim 6, wherein said numerical aperture is such that said reflectance response at said first point approximates said reflectance response for said entire first line and said reflectance response at said second point approximates said reflectance response for said entire second line.

8. The method of claim 7, wherein when said numerical is approximately 0.1 or less.

9. The method of claim 6, wherein the step of determining said first point and said second point includes determining said first point at a center of said first line and determining said second point at a center of said second line.

10. The method of claim 1, wherein the step of determining said first point and said second point includes determining said first point along a first line parallel to said two-dimensional grating structure and determining said second point along a second line parallel to said two-dimensional grating structure.

11. The method of claim 10, wherein said numerical aperture is such that said reflectance response at said first point approximates said reflectance response for said entire first line and said reflectance response at said second point approximates said reflectance response for said entire second line.

12. The method of claim 11, wherein when said numerical aperture is approximately 0.1 or less.

13. The method of claim 10, wherein the step of determining said first point and said second point includes determining said first point at a center of said fist line and determining said second point at a center of said second line.

14. The method of claim 1, wherein said determining characteristics comprise a first weight of said light intensity distribution at said first point and a second weight of said light intensity distribution at said point.

15. The method of claim 14, wherein the step of determining said approximated integrated reflectance response includes using the following equation:

$$w_1 R(x_1) + w_2 R(x_2)$$

where, $x_1$=a location of said first point;

$x_2$=a location of aid second point;

$w_1$=said weight of said light intensity distribution at said first point;

$w_2$=said weight of said light intensity distribution at said second point;

$R(x_1)$=said simulated reflectance response of light incident at said first point; and $R(x_2)$=said simulated reflectance response of light incident at said second point.

16. The method of claim 1, wherein said light intensity distribution across said aperture is uniform.

17. The method of claim 1, wherein said light intensity distribution across said aperture is not uniform.

18. A computer-readable storage medium containing computer executable code for simulating an integrated response an aperture within an optical system from light reflected off of a two-dimensional grating structure by a computer to operate as follows:

determine a first and second point within said aperture;

simulate a reflectance response of said light incident only at said first point and said second point; and determine an approximated integrated reflectance response of said aperture based on said reflectance response only at said first point and said second point and determined characteristic of said optical system.

19. The computer readable storage medium of claim 18, wherein said computer is further instructed to:

obtain the numerical aperture of said optical system;

obtain the light intensity distribution across said aperture; and use a set of orthonormal function to approximate a reflectance response for any wavelength from said two-dimensional grating structure.

20. The computer readable storage medium of claim 19, where said orthonormal function is one of a polynormal or a Fourier series.

21. The computer readable storage medium of claim 20, wherein said orthonormal function is one of a $(4k-2)^{th}$ even polynomial function.

22. The computer readable storage medium of claim 21, wherein k is a value sufficient such that when used, said $(4k-2)^{th}$ even polynomial function approximates said reflectance response for said resulting wavelength.

23. The computer readable storage medium of claim 18, wherein said executable code instructs said computer to determine said first point along a first line substantially parallel to said two-dimensional grating structure and to determine said second point along a second line substantially parallel to said two-dimensional grating structure.

24. The computer readable storage medium of claim 23, wherein said numerical aperture is such that said reflectance response at said first point approximates said reflectance response for said entire first line and said reflectance response at said second point approximates said reflectance response for said entire second line.

25. The computer readable storage medium of claim 24, wherein when said numerical aperture is approximately 0.1 or less.

26. The computer readable storage medium of claim 23, wherein the step of determining said first point and said second point includes determining said first point at a center of said first line and determining said second point at a center of said second line.

27. The computer readable storage medium of claim 18, wherein said executable code instructs said computer to determine said first point along a first line parallel to said two-dimensional grating structure and to determine said second point along a second line parallel to said two-dimensional grating structure.

28. The computer readable storage medium of claim 27, wherein said numerical aperture is such that said reflectance response at said first point approximates said reflectance response for said entire first line and said reflectance response at said second point approximates said reflectance response for said entire second line.

29. The computer readable storage medium of claim 28, wherein when said numerical said approximately 0.1 or less.

30. The computer readable storage medium of claim 27, wherein the step of determining said first point and said second point includes determining said first point at a center of said first line and determining said second point at a center of said second line.

31. The computer readable storage medium of claim 18, wherein said determined characteristics comprise a first weight of said response at said first point and a second weight of said response at said second point.

32. The computer readable storage medium of claim 31, wherein said approximated integrated reflectance response is determined by using the following equation:

$$w_1 R(x_1) + w_2 R(x_2)$$

where, $x_1$=a location of said first point;

$x_2$=a location of said second point;

$w_1$=said weight of said light intensity distribution at said first point;

$w_2$=said weight of said light intensity distribution at said second point;

$R(x_1)$=said simulated reflectance response of light incident at said first point; and $R(x_2)$=said simulated reflectance response of light incident at said second point.

33. The computer readable storage medium of claim 18, wherein said light intensity distribution is uniform across said aperture.

34. The computer readable storage medium of claim 18, wherein said light intensity distribution is not uniform across said aperture.

35. A system for determining an integrated response across an aperture within an optical system from light reflected off of a two-dimensional grating structure, comprising:

a device for determining a first and second point within said aperture;

a device for simulating a reflectance response of said light incident only at said first point and said second point; and a device for determining an approximated integrated reflectance response of said aperture based on said reflectance response only at said first point and said second point and a weight of said light intensity distribution incident at said first point and said second point.

36. The system of claim 35, further comprising:

means for obtaining the numerical of said optical system;

means for obtaining the light intensity distribution across said aperture; and means for using a set of orthonormal functions to approximate a reflectance response for any wavelength from said two-dimensional grating structure.

37. The system of claim 36, where said orthonormal function is one of a polynomial or a Fourier series.

38. The system of claim 37, wherein said orthonormal function is one of a $(4k-2)^{th}$ even polynomial function.

39. The system of claim 38, wherein k is a value sufficient such that when used, said $(4k-2)^{th}$ even polynormal function approximates said reflectance response for said resulting wavelength.

40. The system of claim 35, wherein the step of determining said first point and said second point includes determining said first point along a first line substantially parallel to said two-dimensional grating structure and determining said second point along a second line substantially parallel to said two-dimensional grating structure.

41. The system of claim 40, wherein said numerical aperture is such that said reflectance response at said first point approximates said reflectance response for said entire first line and said reflectance response at said second point approximates said reflectance response for said entire second line.

42. The system of claim 41, wherein when said numerical aperture is approximately 0.1 or less.

43. The system of claim 40, wherein the step of determining said first point and said second point includes determining said first point at a center of said first line and determining said second point at a center of said second line.

44. The system of claim 35, wherein the step of determining said first point and said second point includes determining said first point along a first line parallel to said two-dimensional grating structure and determining said second point along a second line parallel to said two-dimensional grating structure.

45. The system of claim 41, wherein said numerical aperture is such that said reflectance response at said first point approximates said reflectance response for said entire first line and said reflectance response at said second point approximates said reflectance response for said entire second line.

46. The system of claim 45, wherein when said numerical aperture is approximately 0.1 or less.

47. The system of claim 44, where the step of determining said first point and said second point includes determining said first point at a center of said first line and determining said second point at a center of said second line.

48. The system of claim 35, wherein said determining characteristics comprise a first weight of said response at said first point and a second weight of said response at said second point.

49. The system of claim 48, wherein said device for determining said approximated integrated reflectance response uses the following equation:

$$w_1 R(x_1) + w_2 R(x_2)$$

where, $x_1$=a location of said first point;

$x_2$=a location of said second point;

$w_1$=said weight of said light intensity distribution at said first point;

$w_2$=said weight of said light intensity distribution at said second point;

$R(x_1)$=said simulated reflectance response of light incident at said first point; and $R(x_2)$=said simulated reflectance response of light incident at said second point.

50. The system of claim 35, wherein said light intensity distribution across said aperture is uniform.

51. The system of claim 35, wherein said light intensity distribution across said a is not uniform.

* * * * *